US008753807B2

(12) United States Patent
Wieland et al.

(10) Patent No.: US 8,753,807 B2
(45) Date of Patent: *Jun. 17, 2014

(54) METHOD FOR MICROBES DEPLETION IN HUMAN BLOOD OR FULL SERUM USING ANTIMICROBIAL PHOTODYNAMIC LASER THERAPY

(75) Inventors: Gerhard D. Wieland, Jena (DE); Albrecht Volker, Bergholz Rehbrücke (DE); Karl-Heinz Völpel, Kahla (DE); Burkhard Gitter, Jena (DE)

(73) Assignee: Biolitec Pharma Marketing Ltd, F.T. Labuan (MY)

( * ) Notice: Subject to any disclaimer, the term of this patent is extended or adjusted under 35 U.S.C. 154(b) by 0 days.

This patent is subject to a terminal disclaimer.

(21) Appl. No.: 13/375,799

(22) PCT Filed: Jun. 2, 2010

(86) PCT No.: PCT/US2010/037044
§ 371 (c)(1),
(2), (4) Date: Dec. 2, 2011

(87) PCT Pub. No.: WO2010/141564
PCT Pub. Date: Dec. 9, 2010

(65) Prior Publication Data
US 2012/0094269 A1    Apr. 19, 2012

Related U.S. Application Data

(60) Provisional application No. 61/183,263, filed on Jun. 2, 2009.

(51) Int. Cl.
*A01N 1/02* (2006.01)

(52) U.S. Cl.
USPC .............................................................. 435/2

(58) Field of Classification Search
None
See application file for complete search history.

(56) References Cited

U.S. PATENT DOCUMENTS 6,843,961 B2 * 1/2005 Hlavinka et al. ................ 422/24
2004/0256329 A1 * 12/2004 Meserol et al. ............... 210/748

* cited by examiner

*Primary Examiner* — Suzanne M Noakes
*Assistant Examiner* — Stephen Chong
(74) *Attorney, Agent, or Firm* — Bolesh J. Skutnik; B J Associates

(57) ABSTRACT

Treatment methods/devices are provided for attenuating/inactivating the pathogenic microbes found in biological fluids e.g. blood/blood products including human single-donor-fresh-frozen-plasma, platelet concentrate, red blood cells, blood clotting factors. An Antimicrobial Photodynamic Therapy method is used to eliminate multiple (resistant) bacteria, viral agents, fungi, parasites and other undetected or non-easily detected pathogenic microbes or particles in blood and blood products without affecting their biological properties. Resistant bacteria are difficult to be eliminated. This is especially true in the case for *S. aureus* and related strains, *Staphylococcus epidermidis* or *Propionibacterium acnes, Borrelia* species and other bacteria found on skin. Further embodiments eliminate undetected or non-easily detected viral agents contaminating blood/blood products responsible for spreading hepatitis, Acquired ImmunoDeficiency Syndrome and other blood borne viral diseases. Human Immunodeficiency, hepatitis B and hepatitis C viruses have emerged as major blood borne infections. Numerous parasites transmitted through bloods and derived products are also eliminated by these processes/devices.

19 Claims, 1 Drawing Sheet

METHOD FOR MICROBES DEPLETION IN HUMAN BLOOD OR FULL SERUM USING ANTIMICROBIAL PHOTODYNAMIC LASER THERAPY

NATIONAL FILING UNDER 35 USC 371

This application is being filed as a US National stage under 35 USC 371 of PCT Application No. PCT/US10/37044, which was filed Jun. 2, 2010 and also claims the benefit of U.S. Provisional Application Ser. No. 61/183,263 filed Jun. 2, 2009, entitled "A Novel Method for Microbial Depletion in Human Blood and Blood Products Using Antimicrobial PhotoDynamic Therapy" by Gerhard Wieland et al., both of which are incorporated by reference herein.

BACKGROUND OF THE INVENTION

1. Field of the Invention

Present invention relates to the destruction, elimination and/or inactivation of pathogenic microbes in biological fluids. In particular, it relates to antimicrobial photodynamic laser therapy method and device to eliminate pathogenic microorganism in biological fluids such as blood and blood products.

2. Invention Disclosure Statement

The spread of blood borne diseases resulting from transfusion of contaminated blood or blood product is recognized as a major medical health problem. Blood is most commonly donated as whole blood by inserting a catheter into a vein and collecting it in a plastic bag (mixed with anticoagulant) via gravity flow. Thus collected blood is then separated into components. Aside from red blood cells, plasma, and platelets, the resulting blood component products also include albumin protein, clotting factor concentrates, cryoprecipitate, fibrinogen concentrate, and immunoglobulins (antibodies). Red cells, plasma and platelets can also be donated individually via a more complex process called aphaeresis.

The importance of blood transfusions is widely known, especially in cases of people who suffer major trauma such as car accidents or in many surgeries that could not be performed without transfusion support. Without enough blood in blood vessels due to acute or massive blood loss there is not enough pressure to push new blood to the tissues, causing organ death because of lack of oxygen. Blood transfusions may also be used to treat severe anemia or thrombocytopenia caused by blood diseases. Another condition requiring frequent blood transfusions is people suffering from hemophilia or sickle-cell disease. Depending on the disease requirements, whole blood or blood products such as fresh frozen plasma, platelet concentrates, red blood cell concentrates and others should be transfused. In any case, to prevent a hazardous recipient's immune reaction transfused blood should be compatible with the components of the recipient's body.

Blood transfusions can be life-saving but, as with any treatment, there are risks involved. Many viruses, parasites, bacteria and/or toxins may be present in human blood and if contaminated blood or blood products are not efficaciously inactivated or the contaminants are not properly eliminated prior to blood transfusion this may cause infectious diseases with high mortality rates. There is a risk that a given blood transfusion will transmit a viral infection to its recipient. The risks of acquiring hepatitis B virus (HBV), Human Immuno-deficiency virus (HIV) or hepatitis C virus (HCV), via blood transfusion are a major health threat even in developed countries like the U.S.

Bacterial resistance against antibiotics makes an infection much harder to treat. Higher doses or stronger drugs may be required to control infections in such cases. In extreme cases, bacterial resistance can be fatal. Antibiotics are powerful bacteria-killing drugs that help our bodies regain the upper hand when a bacterial infection develops. Overuse of broad-spectrum antibiotics, such as second- and third-generation cephalosporins, greatly hastens the development of methicillin resistance.

*Staphylococcus aureus* a Gram Positive bacterium is one of the examples for ever increasingly resistant pathogens. It is to be found on the mucous membranes and the skin also in healthy people. It is extremely adaptable to antibiotic pressure. Resistant strains, also known by the name Methicillin-resistant *Staphylococcus aureus* (MRSA), are responsible for difficult-to-treat infections in humans. Since the strains often happen to be resistant to more than one antibiotic compound it may also be referred to as Multiple-Resistant *Staphylococcus aureus*.

Over a period of time the bacteria generally develop resistance to antibiotics. Along with the present chemical therapy methods; photodynamic therapy—a treatment method against cancerous cells, has been found to be effective in destroying a wide range of microbes. Photodynamic therapy is based on activation of photosensitizer by appropriate wavelength. Photoactivated photosensitizer generates singlet oxygen and free radicals responsible for destruction of abnormal cells. Various photosensitizers have been studied for their bactericidal effect on pathogenic microbes and were found to be effective.

There are many steps taken to obtain uncontaminated donor's blood, nevertheless the major treat comes from the undetected microbial agents which need to be inactivated before blood transfusion. Blood components can be contaminated during any of the many steps of preparation like blood collection, processing, pooling and transfusion. Thus, tested donor's blood apparently healthy might be contaminated with millions of undetected/unknown infectious microbes. Furthermore, donor's blood units may be contaminated by bacteria during storage which will cause potentially fatal infections in the recipient; or may contain remained leukocytes which then release chemicals causing disease or severe fever.

In U.S. Pat. No. 5,660,731, Piechocki, et al. disclose a method, system and device for removal of methylene blue from biological fluid after anti-microbial treatment. In this patent they disclose a treatment protocol using methylene blue for inactivating materials such as virus and bacteria from blood and blood products. It is also discloses the method of separating the methylene blue from the biological fluid using carbon fibers.

Wollowitz, et al. in his U.S. Pat. No. 6,686,480 discloses how Psoralen compounds are used to form covalent crosslinks to the nuclei acid of pathogen for photo-decontamination of pathogen present in blood.

U.S. Pat. No. 5,545,516 by Wagner discloses methods of inactivating pathogenic contaminant in whole blood, plasma, cellular blood components using phenthiazin-5-ium dye(s) and irradiating at 560-800 nm to inactivate all the pathogens.

In U.S. Pat. No. 7,407,948; Griffiths et al. disclose a photosensitive composition named Phonoselenazinium and its use in photodynamic therapy as anti-infective, anti-cancer and sterilizing agent. In one of the embodiments he discloses the use of this composition for inactivating *S. aureus, E. coil* and other microbes under in vitro conditions by administering the required dosage of photosensitizer and irradiating the cells, after incubation, with a 665 nm CeramOptec diode laser.

U.S. Pat. No. 6,843,961 (Hlavinka et al.) discloses a PDT method and apparatus for inactivating contaminants in blood and blood products using photosensitizers and light of suitable wavelength.

In U.S. Pat. No. 7,244,841, Love et al. disclose use of a composition for killing or attenuating the growth of microorganisms by a method which does not comprise exposing the composition to photodynamic therapy light or sonodynamic therapy ultrasound source. The stimulation of the compound is innate.

An entirely different and promising approach is phage therapy. Wilson in his US Application Publication No. 2007/0020241 discloses a composition comprising of a photosensitizer and a bacteriophage. The bacteriophage used as targeting agent is staphylophage. The bacteriophages are conjugated to photoactive agents, which then target the bacteria specifically. The invention is useful to inactivate staphylococci, more particularly MRSA, EMSA, VRSA, hetero-VRSA, VISA or CA-MRSA strains. The phage therapy is a more complicated system. In U.S. application no. 2002/0001590 Kelly et al. use bacteriophages with antibacterial agents like antibiotic and chemotherapeutic agents to inactivate the pathogens.

Sowemimo-Coker et al. in U.S. Pat. No. 6,235,508 disclose a method of inactivating viral and bacterial contaminants using a composition having photosensitizers attached to a blocking agent and at least one halogen substituted or one non-hydrogen bonding ionic moiety or both. The preferred two photoactive compounds are psoralen and coumarin which are made to target the nucleic acid of viri specifically and bind to DNA and RNA covalently after irradiation with UV light or ionizing radiation leading to inactivation of the pathogens. The use of low toxic compounds along with PS and ionizing radiation can be harmful. Psoralens, are photoactive DNA-intercalating compounds and do not produce singlet oxygen.

In U.S. Pat. No. 6,323,012 Ben-Hur et al. disclose a PDT method for treating viral infection by administering 5-aminolevulinic acid to viral infected cells. After a short duration red light is applied to photodynamically activate protoporphyrin IX accumulated in viral infected cells.

In U.S. Pat. No. 7,094,378 Goodrich et al. disclose a method and apparatus for treating and inactivating microorganisms present in biological fluids. The method involves adjusting the percentage of plasma in the fluid to be treated and mixing with photosensitizer (riboflavin) and exposing the fluid to light whereby the microbes are inactivated. Similarly Hlavinka et al., in their U.S. Pat. No. 7,077,559 disclose a mixing system, apparatus and method for pathogen reduction in blood and blood products using riboflavin and light. The squeezing or clamping devices ensure proper photo-irradiation of blood and blood components.

Reddy et al in their U.S. Pat. No. 7,049,110 disclose a PDT method and apparatus for inactivating microorganisms in biological fluids by adding non-toxic PS to the fluid and exposing the fluid to photo-irradiation.

The conventional screening and processing methods used against pathogenic microbes are not found to be very effective in controlling its rapid transmission through contaminated blood and blood products. The method disclosed in prior art for elimination of microbes is not found to be effective in attenuating all the bacterial, viral and other pathogens as claimed. Thus, it is essential to eliminate or inactivate these pathogen materials from blood and blood products before transfusion. Unfortunately, up to now there have been many difficulties to eliminate or inactivate blood pathogens in materials from blood or blood products due to insufficient filtration capacity of devices, antibiotic resistance of difficult-to-treat microbes or lack of an efficient and efficacious device and/or method. Thus, there is a need to provide an efficient and efficacious method and device to eliminate or inactivate pathogenic material from blood and blood products, from single donors without damaging the therapeutic and biological properties of such biological fluids.

OBJECTIVES AND BRIEF SUMMARY OF THE INVENTION

It is an objective of the present invention to provide an Antimicrobial Photodynamic Therapy method and a treatment device for elimination destruction, and/or inactivation of pathogenic microbes to be found in biological fluids such as blood and blood products collected from donors.

It is another objective of the present invention to provide Antimicrobial Photodynamic Therapy method and a treatment device for purification of infected blood and blood products using an effective antimicrobial photosensitizer and light.

It is yet another objective of the present invention to provide an Antimicrobial Photodynamic Therapy method and treatment device having an illumination unit with light source for elimination of undetected viral component contaminating blood and blood products.

It is still another objective of the present invention to provide an Antimicrobial Photodynamic Therapy method and treatment device for eradiation, elimination and/or inactivation of pathogens without altering or affecting the biologic and therapeutic properties of the treated blood and blood products.

It is also an objective of the present invention to provide an antimicrobial photodynamic laser therapy method and device to kill, eliminate and/or inactivate pathogenic material in whole blood and blood products like human fresh frozen plasma, thrombocyte concentrates, red blood cells (RBC) and blood clotting factors (V, VII, IX, X and XIII).

It is also another objective of the present invention to provide suitable light sources having appropriate wavelength to induce the production of singlet oxygen. Possible light sources are chosen from a list comprising of diode laser systems, high power LEDs, white light or other light sources emitting visible light, and even light sources emitting light in near-UV or near-IR.

Briefly stated, innovative treatment methods and devices for attenuating/inactivating the pathogenic microbes found in biological fluids such as blood and blood products including human single-donor-fresh-frozen-plasma, platelet concentrates, red blood cells (RBC), blood clotting factors (e.g. factors V, VII, VII, IX, X and XIII) are provided. An Antimicrobial Photodynamic Therapy method is used to eliminate multiple (resistant) bacteria, viral agents, fungi, parasites and other undetected or non-easily detected pathogenic microbes or particles in blood and blood products without affecting their biological properties. The resistant bacteria are difficult to be eliminated. This is especially true for *S. aureus* and related strains, *Staphylococcus epidermidis* or *Propionibacterium acnes*, *Borrelia* species and other bacteria found on skin. Further embodiments of the present invention eliminate undetected or non-easily detected viral agents contaminating blood and blood products, which are responsible for spreading hepatitis, Acquired Immune-Deficiency Syndrome (AIDS) and other blood borne viral diseases. Human Immune-deficiency Viruses (HIV), hepatitis B and hepatitis C viruses have recently emerged as major blood borne infections. Numerous parasites transmitted through blood and derived products are also eliminated by these novel processes and devices.

The above and other objects, features and advantages of the present invention will become apparent from the following description read in conjunction with the accompanying drawings.

DETAILED DESCRIPTION OF PREFERRED EMBODIMENTS

Figure 1:
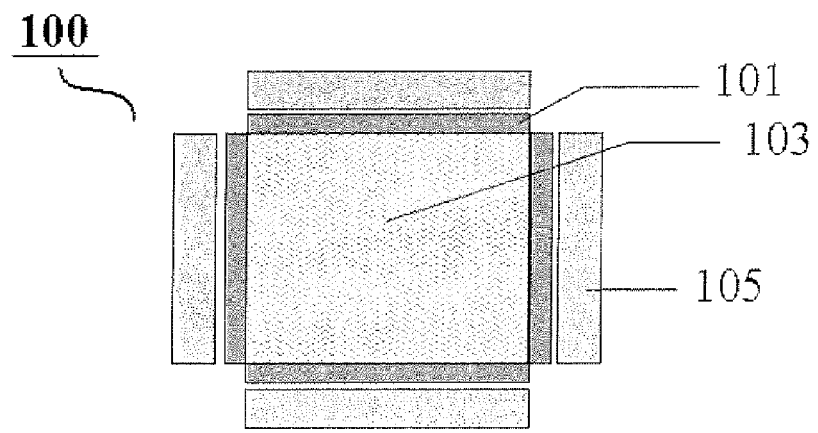
FIG. 1 depicts a top view of a four-fold illumination unit having four LED-ring units.

There are many blood borne, transfusion transmitted and related diseases. Present invention provides an Antimicrobial Photodynamic Therapy method and device for effective elimination, reduction and/or inactivation of pathogenic microorganisms to be found in whole blood and blood products. Whole blood content including red blood cells (RBC), white blood cells (WBC) and platelets are suspended in a fluid called plasma. The terms 'microorganism', 'pathogen', 'microorganism', 'microbial agents' or 'microbe' in this invention include all types of harmful or blood contaminating bacteria and their resistant species, prions, fungi, viri, protozoan and blood parasites causing severe infections in both humans and animals. The terms "blood products" and "blood components" refers to human single-donor-fresh-frozen-plasma, thrombocyte concentrates, platelet pheresis, red blood cells (RBC), white blood cell (WBC), granulocyte concentrates, albumin, cryoprecipitations, antithrombin III, antihemophilic factor (AHF), blood clotting factors (e.g. factors V, VII, VII, IX, X and XIII) and combinations of them. The terms "biological fluid" or "body fluid" refers to whole blood or blood products.

The development of resistances to antibiotics is the major problem faced while treating bacterial infections. Especially multiple-resistant bacteria for e.g. methicillin-susceptible *Staphylococcus aureus* (MSSA) and methicillin-resistant *Staphylococcus aureus* (MRSA) are the most frequently identified antimicrobial drug resistant pathogens in US hospitals. At the same time the real threat in blood donated from apparently healthy donors is corning from skin bacteria like *Staphylococcus epidermidis* or *Propionibacterium acnes*, *Borellia* species and other pathogenic bacteria transmitted in the process of blood donation. The present invention provides a method and device to eliminate such bacterial infesting of biological fluids.

Transfusion Transmitted Virus is a relatively new virus found to contaminate blood. Viral agents like herpes viri, Human immunodeficiency virus (HIV), Hepatitis C virus (HCV) and Hepatitis B Virus (HBV) are found in blood and often go undetected. Other lesser known viral agents include T-cell lymphotropic viruses, cytomegalovirus, and parvovirus. Virus infected blood then is responsible for transmission of blood borne diseases like AIDS, Hepatitis and similar. Eliminating such undetected viri, resistant bacteria and other microbes in biological fluids such as blood and blood products is made possible using the method and device of present invention.

Present invention also aims to eliminate infectious blood-borne protozoan parasites like *Trypanosoma cruzi*, which causes Chagas' disease; the Trypanosoma species causing African sleeping sickness; *plasmodium* species causing malaria, and especially *Plasmodium falciparum* which is responsible for malignant and increasingly drug resistant type of malaria. In addition to this threat, there are also other unknown microbes yet to be identified. The aim in general is to destruct the non-easily detected hazards in blood donated by healthy donors.

Photosensitive agents and their derivates are effectively used as an antimicrobial agent. A preferred photosensitizer, discovered herein, is Safranin O which exists in two tautomeric forms and can be photo activated at 532 nm.

Safranin O exhibits high antimicrobial activity. Safranin O is found to be very effective even in the presence of complex biological fluids like blood, serum etc. While other photosensitizers are used as antimicrobial agents, in the present invention the preferred photosensitizer is selected from the group of phenothiazines, porphyrins, chlorins and others.

In one embodiment, a treatment device for antimicrobial photodynamic therapy comprising an illumination unit, sterile light-transparent container bag(s) and bag holder(s); and a photosensitizer-absorber unit is provided. The illumination unit of the present invention includes light source selected from the group consisting of, but not limited thereby to lasers, diode laser systems, LEDs, high power LEDs, lamps, white light or other light sources having one or more wavelengths absorbed by the selected photosensitizer. The light source operates at appropriate wavelengths including the visible light, near-Ultraviolet (UV) and/or near-Infrared (NIR) region of the electromagnetic spectrum (EMS). The illumination unit uses the light source to induce the production of singlet oxygen while performing the photodynamic therapy. Preferably, the light source comprises LED lamps. Illumination unit further comprises a cooling element and boxes as bag holder(s). Additionally, the illumination unit consists of means for sliding, rotating or a similar action, ensuring proper mixing and exposure of the blood within the container bag to light from illumination unit. It is also well equipped to hold the sterile light-transparent container bag in place during the procedure. The container bag containing blood to be placed in the illumination unit is photo-transparent to allow penetration of light to activate the photosensitizer. Thus, before illumination is performed container bag containing blood is properly covered to avoid early photosensitizer activation. Preferably, sterile light-transparent container bags are connected with the aid of serial or parallel tubes to provide the appropriate illumination dose to the treated biological fluid. The photosensitizer-absorber unit is used to remove the excess, un-reacted or non-activated photosensitizer present in the treated biological fluid. In one embodiment, the photosensitizer-absorber unit consists of a housing filled with porous beads and sponges which extract and/or absorb the excess of or non-activated photosensitizer from treated blood and blood products. Treated and cleansed blood and blood products can be stored for further use.

In another embodiment, an antimicrobial photodynamic therapy (PDT) method for the elimination, eradication and/or inactivation of pathogens from blood and blood products without adversely affecting the essential elements of their biological activity comprises the steps of: 1) collecting blood; 2) separating whole blood in blood components if necessary; 3) mixing a photosensitizer with blood or blood components comprising a treatment fluid; 4) illuminating said treatment fluid; 5) depleting excess and/or non-activated photosensitizer and residual fragments; and 6) collecting and storing the treated and cleansed blood or blood components in a sterile fashion until further use.

In order to prevent blood clotting an anti-coagulation substance like heparin or citrate is added to the collection bag. Preferably, blood and blood components are collected from healthy donors. A centrifuge may be used to hasten the separation step. Separated blood components are then placed into sterile bags and stored, ready for subsequent antimicrobial PDT treatment. Preferred photosensitizer is BLC 2003 (Safranin-O). The existence of an incubation period after or during step 3) ensures a proper mixing of photosensitizer with blood or blood components to be treated. Additionally, a sliding, rotating or similar motion provided by the treatment device allows further mixing between the photosensitizer and blood or blood components and completely illumination of the biological fluid and/or its components. Illumination step is performed with the light source of the treatment device of wavelength coded to the selected photosensitizer is employed. When the photosensitizer used is BLC 2003 the light source preferably operates/includes at 532 nm. The step of depletion of excess and/or non-activated photosensitizer and residual fragments may be done by passing the active microbe-free treatment fluid through a photosensitizer-absorber unit which may also adsorb or absorb residual fragments such as inactivated microbes and alike. Treated blood or blood components may be re-mixed and re-infused into a human or animal fluid stream adjusting all necessary parameters such as temperature, density, composition and others.

The antimicrobial PDT method of present invention does not adversely affect the essential elements of the biological activity of the treated blood or blood products nor shows impairment of their functional capacity after treatment.

The present invention is further illustrated by the following examples, but is not limited thereby.

Example 1

General Treatment Procedure for Microbial Elimination from Blood and Blood Products The general steps for elimination eradication and/or inactivation of pathogens from blood and blood products involves:

Step 1: Involves collection of blood from a healthy donor. Anti-coagulant like heparin or citrate is added to the collection bag to prevent clotting of blood.

Step 2: Separation of the blood components. Blood components include red blood cells, plasma, platelets, and (cryo-precipitated) anti-hemophilic factors (AHF). If blood is treated to prevent clotting and permitted to stand in a container, the red blood cells, which weigh more than the other components, will settle to the bottom; the plasma will stay on top; and the white blood cells and platelets will remain suspended between the plasma and the red blood cells. A centrifuge may be used to hasten this separation process. The platelet-rich plasma is then removed and placed into a sterile bag and can be used to prepare platelets and plasma or cryoprecipitated AHF. To obtain platelets, the platelet-rich plasma is centrifuged, causing the platelets to settle at the bottom. Plasma and platelets are then separated and made available for transfusion. The plasma also may be pooled with plasma from other donors and further processed, or fractionated, to provide purified plasma proteins such as albumin, intravenous immuno-globulin (IVIG), and clotting factors.

Step 3: The sterile light-transparent container bags containing blood and blood products are infused with photosensitizer preferably BLC 2003 (Safranin-O).

Step 4: Ensure proper mixing of photosensitizer and blood and blood products followed by a short incubation period.

Step 5: The sterile light-transparent container bag, containing blood or blood products mixed with photosensitizer, is placed into the treatment device having a bag holder which can be moved in sliding motion. Once the bag is secured to the holder, holder is set into sliding motion. This ensures completely irradiation of blood and its components within the sterile light-transparent container bag.

Step 6: Irradiation at a wavelength (532 nm when BLC2003 is used) coded to the selected photosensitizer.

Step 7: The microbe free fluid then is passed through a photosensitizer-absorber. This absorber unit removes the excess and non-activated photosensitizer present in the treated biological fluid.

Step 8: The cleansed and treated blood/blood component is collected and stored until further use.

Thus treated blood shows neither significant decrease in coagulation factor activities nor is the functional capacity of plasma affected. Present invention can be employed to inactivate pathogens at blood banks, in hospitals or labs.

Example 2

Treatment Device and Antimicrobial PDT Method to Treat Blood and Blood Products

Figure 2:
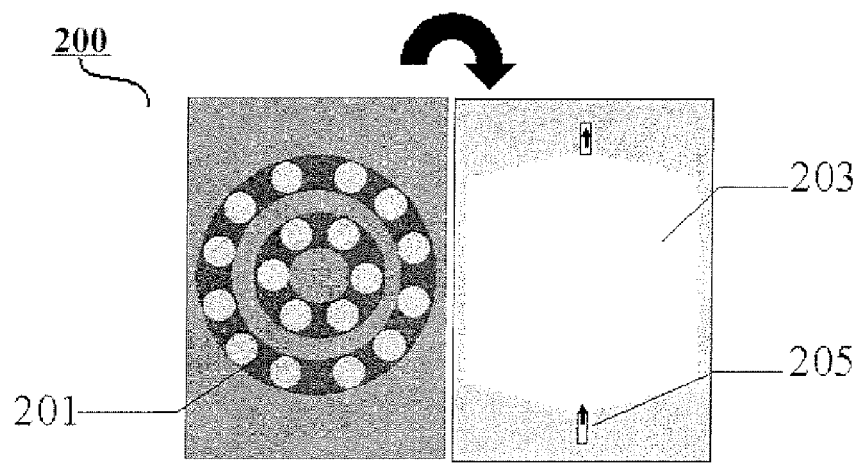
FIG. 2 illustrates an embodiment of an illumination unit with two LED-rings and an illumination bag having connector.

FIG. 1 depicts the top view of a four-fold illumination unit 100 with four LED-ring units 101 on four sides of the rectangular cubical shaped illumination unit. The four LED units are located on cooling element 103 in the centre and having the corresponding boxes 105 containing the sterile light-transparent container bags. The sterile light-transparent container bags are connected by tubes in order to obtain a flow through all four bags and a four-fold illumination LED unit. Each inflow for the sterile light-transparent container bag is located at the bottom side. FIG. 2 shows how each illumination unit is arranged with corresponding sterile light-transparent container bag on each side of four-fold illumination unit 100.

FIG. 2 shows LED unit and the corresponding arrangement of the box and sterile light-transparent container bags to be illuminated within each side of illumination unit 200. Each of the LED units has arrays of high powered LEDs arranged in two concentric rings 201 (Luxeon® Rings with total 18 LED-units with a LED wavelength of 530 nm, when the preferred photosensitizer is used). The arrangement of LEDs can be done in one or more rings and in many different ways. The illumination unit has a corresponding box wherein illumination bag 203 is located, having tube connectors 205. The arrows indicate the flow direction of bacterial suspension.

The infected whole blood from the healthy donor is withdrawn and collected into a sterile citrate or heparin sterile light-transparent container bag. The sterile light-transparent container bag in this invention is specially designed for the illumination unit to be used during antimicrobial photodynamic therapy treatment. Thus collected blood is separated to its respective components by methods already known in the prior art and to the experts in the field or the whole blood as such can be subjected to present treatment method. The photosensitizer agent is added into the photo-transparent sterile bag. The added photosensitizer is mixed to the blood and/or blood components using an orbital shaker to ensure complete exposure of the microbes to photosensitizer. Thus prepared blood bag is now placed into a bag holder found within the illumination unit.

Once the bag is secured into the holder, it is set into a sliding motion. The illumination unit is switched on and the sterile light-transparent container bag in sliding motion is exposed to a specific wavelength matching the absorption spectrum of photosensitizer added for normally prolonged time sufficient to eliminate bacterial and parasitic particles. The photosensitizer accumulates on and in the microbial cells which subsequently are destroyed by a photo-cytotoxic effect. The treated fluid is allowed to pass through a photosensitizer-absorber unit consisting of plastic housing that is filled with tiny porous beads and larger sponges. These beads/sponges extract/absorb the excess of or non-activated photosensitizer from the treated fluid. The excess or unreacted photosensitizer in the treated blood is finally removed. The cleansed blood and blood products can be stored for further use. Thus treated blood and its products are still intact in their biological function and their therapeutic effect is not reduced. The present method and device use in this invention is effectively used to eliminate the microbial pathogens.

This method can be use to eliminate pathogens in biological fluids, which includes but is not limited to whole blood, blood products, and blood components; the term blood component further includes human single-donor-fresh-frozen-plasma, platelet concentrate, red blood cells (RBC), blood clotting factors (e.g. factors V, VII, VII, IX, X and XIII) individually or in combination.

Example 3

Purification and Elimination of Undetected Viral Agents from Donated Blood

Blood transfusions can be life-saving in some situations, such as massive blood loss due to trauma, or can be used to replace blood lost during surgery. Blood transfusions may also be used to treat a severe anemia or thrombocytopenia caused by a blood disease. People suffering from hemophilia or sickle-cell disease may require frequent blood transfusions. Early transfusions used whole blood, while modern medical practice uses only components of the blood. Donated blood is usually subjected to processing after it is collected, to make it suitable for use in specific patient populations. In a number of infectious diseases such as HIV, syphilis, hepatitis and others undetected microbes can be passed from the seemingly healthy blood donor to recipient through blood transfusion. The present invention helps to eliminate undetected or non-easily detected viral agents and provides biological fluids free of pathogenic microbes for safe use. The whole blood collected from patient is mixed with a minuscule amount of a non toxic photosensitizer, preferably Safranin O. The sterile light-transparent container bags containing whole blood and Safranin O is thoroughly mixed using an orbital shaker and placed into a bag holder in illumination unit, set into sliding motion. The illumination unit is provided with light source having a wavelength 532 nm. The light source used can include a laser or high-power LED-light. Light sources emitting light at visible region, near UV and/or near IR can be used in the illumination unit, depending on the absorption characteristics of the selected photosensitizer. Thus bags containing treated blood should be stored in climate controlled chambers until final use in hemodiafiltration/or for other purposes. This normally prolonged time should be sufficient to eliminate viral particles. The excess or non-activated photosensitizer in the treated blood and blood products is removed using photosensitizer-absorber unit/means consisting of plastic housing that is filled with tiny porous beads and larger sponges. These beads extract/absorb the excess or non-activated photosensitizer molecules from the treated biological fluid.

Example 4

Purification and Elimination of Parasites from Donated Blood

Generally considered healthy person's blood may also be contaminated by pathogenic microbes growing under storage conditions especially in platelet concentrates stored at 37° C. The blood has nutrients, sugars, oxygen, providing the perfect environment and temperature for the growth of microorganisms. If the immune system is healthy, parasites are kept in check. The most common protozoan parasites found in blood includes endo-parasites, such as the malarial parasites and trypanosomes, having their infective stages in the host's blood. General known protozoa are *Plasmodium* species causing malaria, another protozoon, *Trypanosoma cruzi*, causing Chagas disease, or American sleeping sickness, and *Trypanosoma brucei* causing African trypanosomiasis. These parasites are found in the blood supply in increasing numbers. The parasites enter fat and muscle cells and begin to multiply, eventually being released into the blood and thus distributed throughout the body. They eventually become quite rare in the blood, but continue to live and multiply in organs. The infection persists indefinitely with live and infectious parasites in both blood and organs. Parasites can be passed on when the bug bites again, this time taking in parasites with its meal and subsequently passing them on to the next person it bites. Parasites can also be passed on via blood transfusions or organ donations. Present invention is effectively employed to eliminate such parasites from blood and blood products making them safe for further use in hospitals and blood banks. The blood collected from the healthy donor is infused with Safranin O, a photosensitizer which can target and after illumination inactivates parasites in the blood fluid. Sterile light-transparent container bag containing the photosensitizer and blood is now placed into an illumination chamber. The bag holder is set into sliding motion to ensure thorough exposure of the bag with blood and photosensitizer to light. The blood and its components are not damaged. The unreacted and any excess photosensitizer in the blood is removed, which is now safe for further use in patients.

The treatment method and device of present invention can be employed to treat either the whole blood, or separated blood components individually as described in the general procedure in example 1.

Having described preferred embodiments of the invention with reference to the accompanying drawings, it is to be understood that the invention is not limited to the precise embodiments, and that those skilled in the art can effect changes and modifications without departing from the scope of the invention as defined in the appended claims.

What is claimed is:

1. An antimicrobial photodynamic therapy method for the depletion, elimination, or inactivation of microbe-infused blood and blood products without adversely affecting the essential elements of their biological activity comprises the steps of:
   a. collecting a blood;
   b. separating whole blood into blood components if necessary;
   c. mixing a photosensitizer with blood or blood components comprising a treatment fluid in a sterile light-transparent container bag;
   d. placing said container bag into a treatment device bag holder;
   e. setting said holder into sliding motion, rotating motion or a combination thereof;

f. illuminating said treatment fluid at a wavelength appropriate for the selected photosensitizer to form active microbe-free treatment fluid;

g. depleting excess and/or un-activated photosensitizer and/or residual fragments by passing the active microbe-free treatment fluid through a photosensitizer-absorber unit comprising a plastic housing filled with tiny porous beads and larger sponges; and h. collecting and storing the treatment fluid, after undergoing steps f and g, in a sterile fashion until further use.

2. The antimicrobial photodynamic therapy method according to claim 1, wherein said microbe includes yin, bacteria, multiple resistant bacteria, methicillin-susceptible *Staphylococcus aureus* (MSSA), protozoan parasites, prions, fungi and other undetected, non-easily detected and unknown pathogens.

3. The antimicrobial photodynamic therapy method according to claim 1, wherein, said microbe-infused blood and blood products comprises whole blood, red blood cells, white blood cell, plasma, platelets, platelet concentrates, platelet pheresis, fresh frozen plasma, cryoprecipitations, cryoprecipitated antihemophilic factors (AHF), human single-donor-fresh-frozen-plasma, granulocyte concentrates, albumin, antithrombin III, blood clotting factors and combinations thereof.

4. The antimicrobial photodynamic therapy method according to claim 1, wherein said photosensitizer is selected from the group consisting of Safranin-O, phenothiazines, porphyrins, and chlorins.

5. The antimicrobial photodynamic therapy method according to claim 1, wherein the said illumination consists of irradiating the said blood and blood products with wavelength matching the absorption spectrum of the administered photosensitizer.

6. The antimicrobial photodynamic therapy method according to claim 1, wherein said residual fragments comprises photosensitizer fragments or inactivated microbes.

7. The antimicrobial photodynamic therapy method according to claim 1, wherein said separation step in blood components is performed by a method selected from the group consisting of dilution, segregation, decanting, centrifugation and combinations thereof.

8. The antimicrobial photodynamic therapy method according to claim 1, wherein said further use includes re-mixing and re-infusing treated blood or blood components in appropriate conditions into a human or animal fluid stream.

9. The antimicrobial photodynamic therapy method according to claim 8, wherein said appropriate conditions means adjusting necessary known physiological parameters including temperature, density or composition.

10. A device for antimicrobial photodynamic therapy treatment, according the method of claim 1, used to deplete microbes from a biological fluid comprising:
   an illumination unit;
   sterile light-transparent container bag(s) and a bag holder(s); and
   a photosensitizer-absorber unit.

11. The device according to claim 10, wherein, said illumination unit comprises a light source, cooling element, bag holders and means for sliding, rotating and performing combined motions.

12. The device according to claim 11, wherein said light source comprises high powered light sources.

13. The device according to claim 11, wherein said light source in illumination unit is laser, diode laser system, high power LEDs, lamp, LEDs, white light and other light source having wavelength of visible, near UV and near IR region of electromagnetic spectrum, compatible with preselected photosensitizer.

14. The device according to claim 12, wherein said light source comprises high powered LED source operating at 532 nm.

15. The device according to claim 11, wherein said sliding, rotating and combined motion ensure proper biological fluid-photosensitizer mixing and exposure to light from illumination unit.

16. The device according to claim 10, wherein, said bag holder can slide in motion.

17. The device according to claim 10, wherein, said sterile light-transparent container bag is allows penetration of light to activate the photosensitizer.

18. The device according to claim 10, wherein, said photosensitizer-absorber unit is designed to remove excess and unreacted photosensitizer and residual fragments from treated blood and blood products.

19. The device according to claim 18, wherein, said residual fragments comprises photosensitizer fragments, inactivated microbes and similar fragmented substances present after treating blood and blood products.

* * * * *